US008569539B2

(12) United States Patent
May et al.

(10) Patent No.: US 8,569,539 B2
(45) Date of Patent: Oct. 29, 2013

(54) PROCESS FOR PREPARING ALPHA-HYDROXYCARBOXYLIC ESTERS

(75) Inventors: Alexander May, Darmstadt (DE); Bernd Vogel, Wiesbaden (DE); Hermann Siegert, Seeheim-Jugenheim (DE); Jochen Ackermann, Muehltal (DE); Soenke Broecker, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 444 days.

(21) Appl. No.: 12/298,034

(22) PCT Filed: Mar. 28, 2007

(86) PCT No.: PCT/EP2007/052951
§ 371 (c)(1),
(2), (4) Date: Oct. 22, 2008

(87) PCT Pub. No.: WO2007/131829
PCT Pub. Date: Nov. 22, 2007

(65) Prior Publication Data
US 2009/0182167 A1    Jul. 16, 2009

Related U.S. Application Data

(60) Provisional application No. 60/893,788, filed on Mar. 8, 2007.

(30) Foreign Application Priority Data

May 15, 2006   (DE) .......................... 10 2006 022 896
Mar. 8, 2007   (DE) .......................... 10 2007 011 706

(51) Int. Cl.
*C07C 67/20*     (2006.01)

(52) U.S. Cl.
USPC ............................................... 560/179

(58) Field of Classification Search
CPC ..................................................... C07C 67/20
See application file for complete search history.

(56) References Cited

U.S. PATENT DOCUMENTS

| | | | |
|---|---|---|---|
| 4,055,590 A * | 10/1977 | Gruber et al. ............. | 560/179 |
| 6,310,236 B1 | 10/2001 | Nakamura et al. | |
| 6,743,407 B2 | 6/2004 | Schaefer et al. | |
| 6,977,310 B2 | 12/2005 | Ackermann et al. | |
| 6,979,432 B2 | 12/2005 | Schaefer et al. | |
| 7,288,402 B2 | 10/2007 | Osswald et al. | |
| 7,491,521 B2 | 2/2009 | Osswald et al. | |
| 2006/0211880 A1 | 9/2006 | Ackerman et al. | |
| 2008/0194862 A1 | 8/2008 | Ackermann et al. | |
| 2008/0194875 A1 | 8/2008 | Ackermann et al. | |
| 2008/0248538 A1 | 10/2008 | Osswald et al. | |
| 2008/0269431 A1 | 10/2008 | Sarcinelli et al. | |
| 2009/0118533 A1 | 5/2009 | Broell et al. | |
| 2011/0034728 A1 | 2/2011 | May et al. | |
| 2011/0306784 A1 | 12/2011 | May et al. | |

FOREIGN PATENT DOCUMENTS

| | | |
|---|---|---|
| DE | 25 28 524 | 11/1976 |
| EP | 0 945 423 | 9/1999 |
| JP | 58055444 | 4/1983 |
| JP | 2000-169432 A | 6/2000 |
| TW | 442466 | 6/2001 |

OTHER PUBLICATIONS

U.S. Appl. No. 12/593,090, filed Sep. 25, 2009, Marx, et al.
U.S. Appl. No. 12/602,593, filed Dec. 1, 2009, Marx, et al.
U.S. Appl. No. 12/298,034, filed Oct. 22, 2008, May, et al.
U.S. Appl. No. 12/300,189, filed Nov. 10, 2008, Broell, et al.
U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May, et al.
U.S. Appl. No. 12/443,784, filed Mar. 31, 2009, Vogel, et al.
U.S. Appl. No. 12/442,415, filed Mar. 23, 2009, Vogel, et al.
U.S. Appl. No. 12/303,161, filed Dec. 2, 2008, Marx, et al.
Combined Office Action and Search Report issued Mar. 5, 2013, in Taiwanese Patent Application No. 096116683 (English-language translation only).
Office Action issued Nov. 2, 2012 in Japanese Patent Application No. 2009-510374 submitting German translation only.
Office Action issued Apr. 8, 2013, in Canadian Patent Application No. 2,652,315.
English translation of the International Preliminary Report on Patentability and Written Opinion of the International Searching Authority issued Dec. 10, 2008, in PCT/EP2007/052951.

\* cited by examiner

*Primary Examiner* — Paul A Zucker
(74) *Attorney, Agent, or Firm* — Oblon, Spivak, McClelland, Maier & Neustadt, L.L.P.

(57) ABSTRACT

Alpha-hydroxycarboxylic esters are prepared by a continuous process in which alpha-hydroxycarboxamide is reacted with an alcohol in the presence of a catalyst to obtain a product mixture which contains alpha-hydroxycarboxylic ester, ammonia, unconverted alpha-hydroxycarboxamide and alcohol, and catalyst; wherein reactant streams containing an alpha-hydroxycarboxamide, an alcohol and a catalyst are fed into a pressure reactor. The reactant streams are reacted with one another in the pressure reactor at a pressure in the range of 1 bar to 100 bar; and the product mixture is depleted in alcohol and ammonia by distilling off ammonia at a pressure which is constantly kept greater than 1 bar without the aid of additional stripping media. The continuous process can be employed particularly advantageously on the industrial scale.

37 Claims, 2 Drawing Sheets

PROCESS FOR PREPARING ALPHA-HYDROXYCARBOXYLIC ESTERS

BACKGROUND OF THE INVENTION

1. Field of the Invention

The present invention relates to processes for preparing alpha-hydroxycarboxylic esters on the industrial scale. In particular, the invention relates to a continuous process for preparing alpha-hydroxycarboxylic esters according to the preamble of claim 1.

2. Discussion of the Background

Alpha-hydroxycarboxylic esters are valuable intermediates in the industrial-scale synthesis of acrylic esters and methacrylic esters, referred to hereinafter as alkyl (meth)acrylates. Alkyl (meth)acrylates in turn find their main field of use in the preparation of polymers and copolymers with other polymerizable compounds.

An overview of the common processes for preparing (meth)acrylic esters can be found in the literature, such as Weissermel, Arpe "Industrielle organische Chemie" [Industrial Organic Chemistry], VCH, Weinheim 1994, 4th edition, p. 305 ff. or Kirk Othmer "Encyclopedia of Chemical Technology", 3rd edition, Vol. 15, page 357.

When the aim is the synthesis of methacrylic esters, for example methyl methacrylate, methyl 2-hydroxyisobutyrate (=MHIB), as the alpha-hydroxycarboxylic ester, is a central intermediate for its preparation.

The preparation of alpha-hydroxycarboxylic esters via the reaction of an alcohol with an alpha-hydroxycarboxamide is detailed by way of example in the publication DE-A-24 54 497. This publication describes the use of lead compounds in order to catalyse the reaction. In this context, mention is also made of continuous processes but without providing a technical solution in which the products are obtained with high efficiency.

Furthermore, the document DE-A-25 28 524 describes processes for preparing alpha-hydroxycarboxylic esters. In this context, various catalysts are used, which include lanthanum compounds among others. Although DE-A-25 28 524 also mentions that the processes described can be performed continuously, this publication also does not provide a satisfactory solution to the problems which occur here.

A process of this type is known from EP 0 945 423. Here, a process for preparing alpha-hydroxycarboxylic esters is disclosed, which comprises the steps of reacting an alpha-hydroxycarboxamide and an alcohol in the presence of a catalyst in a liquid phase, while the ammonia concentration in the reaction solution is kept at 0.1% by weight or less by removing ammonia formed as a gas in a gas phase.

To remove the ammonia from the reaction solution as a gas into the gas phase, it is distilled out of the reaction solution. To this end, the reaction solution is heated to boiling, and/or a stripping gas, i.e. an inert gas, is bubbled through the reaction solution.

The disadvantages of the process disclosed in EP 0 945 423 for the preparation of alpha-hydroxycarboxylic esters by alcoholysis of corresponding alpha-hydroxycarboxamides can be summarized as follows:

i. Simply distilling off the ammonia in a process variant disclosed in EP 0 945 423 is relatively ineffective. The implementation of this proposal requires an extremely effective separating column and hence an exceptional level of technical complexity.

ii. When an inert stripping gas is used additionally or exclusively, the effectiveness of the ammonia removal is improved, but at the expense of a further process component, whose handling means additional complexity.

iii. When alpha-hydroxyisobutyramide and methanol are used as reactants, ammonia and residual methanol formed under the conditions disclosed in EP 0 945 423 can be separated from one another only with very great difficulty.

The fact that it is almost always necessary to use an inert gas for ammonia removal and the associated additional handling of a further stream (stripping gas/ammonia separation) make the procedure proposed economically relatively uninteresting, which is also reflected by the lack of an industrial implementation of the process disclosed to date.

SUMMARY OF THE INVENTION

In view of the prior art, it is thus an object of the present invention to provide processes for preparing alpha-hydroxycarboxylic esters, which can be performed in a simple and inexpensive manner.

It is a further object of the invention to provide a process in which the alpha-hydroxycarboxylic esters can be obtained very selectively.

In addition, it was an object of the present invention to provide a process for preparing alpha-hydroxycarboxylic esters, in which no by-products or only small amounts of by-products are obtained. At the same time, the product should be obtained, as far as possible, in high yields and, viewed overall, with low energy consumption.

This object and further objects which are not stated explicitly but which can be derived or discerned immediately from the connections discussed herein by way of introduction are achieved by processes having all features of claim 1. Appropriate modifications of the processes according to the invention are protected in the dependent claims referring back to claim 1.

The present invention accordingly provides continuous processes for preparing alpha-hydroxycarboxylic esters, in which the reactants reacted are alpha-hydroxycarboxamide with an alcohol in the presence of a catalyst to obtain a product mixture which comprises alpha-hydroxycarboxylic ester, ammonia, unconverted alpha-hydroxycarboxamide and alcohol, and catalyst; where the process is characterized in that reactant streams comprising, as reactants, an alpha-hydroxycarboxamide, an alcohol and a catalyst are fed into a pressure reactor;

the reactant streams are reacted with one another in the pressure reactor at a pressure in the range of greater than 1 bar to 100 bar; and the product mixture is depleted in alcohol and ammonia by distilling off ammonia at a pressure which is constantly kept greater than 1 bar without the aid of additional stripping media.

DETAILED DESCRIPTION OF THE INVENTION

The inventive measures can achieve the following advantages among others:

Surprisingly, the ammonia resulting from the inventive reaction can be removed with a relatively low level of complexity and easily from the alcohol, for example methanol, which is used for the alcoholysis or methanolysis of the alpha-hydroxycarboxamide. This is possible even though alcohol, i.e. methanol, and ammonia in dissolved form can be separated from one another only with very great difficulty under customary conditions.

In the separation, ammonia is obtained already in very pure form and can thus be reused in various processes without a further purification step. The alcohol is also obtained such that it is present in a quality suitable for processes and is recyclable, for example, into a preparation process.

At the same time, the process of the invention avoids the use of assistants for the removal of the ammonia; in particular, the use of inert gases as stripping media for the ammonia becomes unnecessary. Accordingly, in the process according to the invention, no relatively large amount of additional inert gas stream is obtained, which would in turn have to be removed from the ammonia.

The process according to the invention affords the alpha-hydroxycarboxylic esters in high yields and purities. This is especially true in comparison with the processes described in EP-A-0945423, in which the α-hydroxycarboxamides are subjected to an alcoholysis to the alpha-hydroxycarboxylic esters while maintaining a very low current ammonia concentration in the liquid phase. Surprisingly, it has been found that the use of pressure in combination with a simple distillation/rectification not only allows the additional measure of stripping with inert gas to be dispensed with but also makes a higher ammonia concentration in the liquid phase tolerable without dispensing with higher selectivities overall.

At the same time, the formation of by-products is unusually low. In addition, especially taking account of the high selectivity, high conversions are achieved.

The process of the present invention also has an extremely low tendency to form by-products.

In addition, the process according to the invention can be performed inexpensively, especially with a low energy demand. At the same time, the catalysts used for the alcoholysis of the alpha-hydroxycarboxamide can be used over a long period without the selectivity or the activity decreasing. In this respect, the catalysts have a high lifetime.

Finally, the process of the present invention can be performed particularly advantageously on the industrial scale.

In the process of the invention, alpha-hydroxycarboxylic esters are prepared by the reaction between the alpha-hydroxycarboxamide and alcohol reactants in the presence of a catalyst.

The alpha-hydroxycarboxamides used in the reaction of the invention include typically all of those carboxamides which have at least one hydroxyl group in the alpha position to the carboxamide group.

Carboxamides in turn are common knowledge in the technical field. Typically, these are understood to mean compounds having groups of the formula —CONR'R"—, in which R' and R" are each independently hydrogen or a group having 1-30 carbon atoms, which comprises in particular 1-20, preferably 1-10 and in particular 1-5 carbon atoms. The carboxamide may comprise 1, 2, 3, 4 or more groups of the formula —CONR'R"—. These include in particular compounds of the formula R(—CONR'R")$_n$ in which the R radical is a group having 1-30 carbon atoms, which in particular has 1-20, preferably 1-10, in particular 1-5 and more preferably 2-3 carbon atoms, R' and R" are each as defined above and n is an integer in the range of 1-10, preferably 1-4 and more preferably 1 or 2.

The expression "group having 1 to 30 carbon atoms" denotes radicals of organic compounds having 1 to 30 carbon atoms. In addition to aromatic and heteroaromatic groups, it also includes aliphatic and heteroaliphatic groups, for example alkyl, cycloalkyl, alkoxy, cycloalkoxy, cycloalkylthio and alkenyl groups. The groups mentioned may be branched or unbranched.

According to the invention, aromatic groups denote radicals of mono- or polycyclic aromatic compounds having preferably 6 to 20, in particular 6 to 12, carbon atoms.

Heteroaromatic groups denote aryl radicals in which at least one CH group has been replaced by N and/or at least two adjacent CH groups have been replaced by S, NH or O.

Aromatic or heteroaromatic groups preferred in accordance with the invention derive from benzene, naphthalene, biphenyl, diphenyl ether, diphenylmethane, diphenyldimethylmethane, bisphenone, diphenyl sulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzothiadiazole, benzopyrazole, benzothiadiazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzooxadiazole, benzopyridine, benzopyrazine, benzopyrazidine, benzopyrimidine, benzotriazine, indolizine, pyridopyridine, imidazopyrimidine, pyrazinopyrimidine, carbazole, aciridine, phenazine, benzoquinoline, phenoxazine, phenothiazine, acridizine, benzopteridine, phenanthroline and phenanthrene, each of which may also optionally be substituted.

The preferred alkyl groups include the methyl, ethyl, propyl, isopropyl, 1-butyl, 2-butyl, 2-methylpropyl, tert-butyl, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and the eicosyl group.

The preferred cycloalkyl groups include the cyclopropyl, cyclobutyl, cyclopentyl, cyclohexyl, cycloheptyl and the cyclooctyl group, each of which is optionally substituted by branched or unbranched alkyl groups.

The preferred alkenyl groups include the vinyl, allyl, 2-methyl-2-propenyl, 2-butenyl, 2-pentenyl, 2-decenyl and the 2-eicosenyl group.

The preferred heteroaliphatic groups include the aforementioned preferred alkyl and cycloalkyl radicals in which at least one carbon unit has been replaced by O, S or an NR$^8$ or NR$^8$R$^9$ group, and R$^8$ and R$^9$ are each independently an alkyl group having 1 to 6 carbon atoms, an alkoxy group having 1 to 6 carbon atoms or an aryl group.

According to the invention, the carboxamides most preferably have branched or unbranched alkyl or alkoxy groups having 1 to 20 carbon atoms, preferably 1 to 12, appropriately 1 to 6, in particular 1 to 4 carbon atoms, and cycloalkyl or cycloalkyloxy groups having 3 to 20 carbon atoms, preferably 5 to 6 carbon atoms.

The R radical may have substituents. The preferred substituents include halogens, especially fluorine, chlorine, bromine, and alkoxy or hydroxyl radicals.

The alpha-hydroxycarboxamides may be used in the process of the invention individually or as a mixture of two or three or more different alpha-hydroxycarboxamides. Particularly preferred alpha-hydroxycarboxamides include alpha-hydroxyisobutyramide and/or alpha-hydroxyisopropionamide.

It is also of particular interest, in a modification of the process according to the invention, to use those alpha-hydroxycarboxamides which are obtainable by cyanohydrin synthesis from ketones or aldehydes and hydrocyanic acid. In a first step, the carbonyl compound, for example a ketone, in particular acetone, or an aldehyde, for example acetaldehyde, propanal, butanal, is reacted with hydrocyanic acid to give the particular cyanohydrin. Particular preference is given to reacting acetone and/or acetaldehyde in a typical manner using a small amount of alkali or of an amine as a catalyst. In a further step, the cyanohydrin thus obtained is reacted with water to give the alpha-hydroxycarboxamide.

This reaction is typically performed in the presence of a catalyst. Suitable catalysts for this purpose are in particular manganese oxide catalysts, as described, for example, in EP-A-0945429, EP-A-0561614 and EP-A-0545697. The manganese oxide may be used in the form of manganese dioxide, which is obtained by treating manganese sulphate with potassium permanganate under acidic conditions (cf. Biochem. J., 50, p. 43 (1951) and J. Chem. Soc., 1953, p. 2189, 1953) or by electrolytic oxidation of manganese sulphate in aqueous solution. In general, the catalyst is used in many cases in the form of powder or granule with a suitable particle size. In addition, the catalyst may be applied to a support. In particular, it is also possible to use so-called slurry reactors or fixed bed reactors, which may also be operated as a trickle bed and are described, inter alia, in EP-A-956 898. In addition, the hydrolysis reaction may be catalysed by enzymes. The suitable enzymes include nitrile hydratases. This reaction is described by way of example in "Screening Characterization and Application of Cyanide-resistant Nitrile Hydratases" Eng. Life. Sci. 2004, 4, No. 6. In addition, the hydrolysis reaction can be catalysed by acids, especially sulphuric acid. This is detailed, inter alia, in JP Hei 4-193845.

The alcohols usable with success in processes of the invention include all alcohols which are familiar to those skilled in the art and precursor compounds of alcohols which, under the given conditions of pressure and temperature, are capable of reacting with the alpha-hydroxycarboxamides in an alcoholysis. Preference is given to converting the α-hydroxycarboxamide by alcoholysis with an alcohol, which comprises preferably 1-10 carbon atoms, more preferably 1 to 5 carbon atoms. Preferred alcohols include methanol, ethanol, propanol, butanol, especially n-butanol and 2-methyl-1-propanol, pentanol, hexanol, heptanol, 2-ethylhexanol, octanol, nonanol and decanol. The alcohol used is more preferably methanol and/or ethanol, methanol being very particularly appropriate. It is also possible in principle to use precursors of an alcohol. For example, alkyl formates may be used. Methyl formate or a mixture of methanol and carbon monoxide are especially suitable.

In the context of the invention, the reaction between alpha-hydroxycarboxamide and alcohol is performed in a pressure reactor. In principle, this is understood to mean a reaction chamber which permits an elevated pressure to be maintained during the reaction. In this context, elevated pressure means a pressure greater than atmospheric pressure, i.e., in particular, greater than 1 bar. In the context of the invention, the pressure may be within a range of greater than 1 bar to less than or equal to 100 bar. It inevitably follows from the statements made that the pressure, both during the inventive reaction/alcoholysis of the alpha-hydroxycarboxamide and during the removal of the ammonia from the product mixture, is greater than atmospheric pressure or greater than 1 bar. In particular, this means that the ammonia formed in the reaction is also distilled out of the mixture under a pressure of greater than 1 bar, while completely dispensing with the use of assistants such as stripping gas for the distillative removal of the ammonia.

In the context of the invention, the product mixture is depleted not only in ammonia but also in unconverted alcohol. Specifically in the case that methanol is used for the alcoholysis, the result is a product mixture comprising, inter alia, the components ammonia and methanol which are in principle very difficult to separate from one another. In the simplest case, the product mixture is depleted in ammonia and alcohol by removing said two components directly as a substance mixture from the product mixture. The two substances are then subjected to a downstream separating operation, for example to a rectification. On the other hand, it is also possible in the context of the invention to remove the two components alcohol (methanol) and ammonia from the product mixture in one operation and at the same time also to separate the two constituents ammonia and alcohol (methanol) from one another.

In a preferred process modification of the invention, it may be of particular interest that the reaction step and the removal of the ammonia/alcohol from the product mixture are separated spatially from one another and performed in different units. For this purpose, for example, one or more pressure reactors can be provided and these can be connected with a pressure distillation column. These are one or more reactors which are arranged outside the distillation/reaction column in a separate region.

In the widest sense, this includes continuous processes for preparing alpha-hydroxycarboxylic esters in which the reactants reacted are alpha-hydroxycarboxamide with an alcohol in the presence of a catalyst to obtain a product mixture which comprises alpha-hydroxycarboxylic ester, ammonia, unconverted alpha-hydroxycarboxamide and alcohol, and catalyst; the process being characterized in that
a) reactant streams comprising, as reactants, an alpha-hydroxycarboxamide, an alcohol and a catalyst are fed into a pressure reactor;
b) the reactant streams are reacted with one another in the pressure reactor at a pressure in the range of greater than 1 bar to 100 bar;
c) the product mixture resulting from step b), comprising alpha-hydroxycarboxylic ester, unconverted alpha-hydroxycarboxamide and catalyst, is discharged from the pressure reactor; and
d) the product mixture is depleted in alcohol and ammonia by distilling off ammonia at a pressure which is constantly kept greater than 1 bar.

According to the statements made above, a particularly appropriate process modification envisages that
b1) the reactants are reacted with one another in the pressure reactor at a pressure in the range of 5 bar to 70 bar;
b2) the product mixture resulting from step b1) is decompressed to a pressure lower than the pressure in the pressure reactor and greater than 1 bar;

c1) the decompressed product mixture resulting from step b2) is fed into a distillation column;
c2) ammonia and alcohol are distilled off via the top in the distillation column, the pressure in the distillation column being kept within the range of greater than 1 bar to less than or equal to 10 bar; and
d1) the product mixture which results from step c2), has been depleted in ammonia and alcohol and comprises alpha-hydroxycarboxylic ester, unconverted alpha-hydroxycarboxamide and catalyst is discharged from the column.

In this process variant, reaction of the reactants and removal of ammonia/alcohol take place in two different spatially separate units. In other words, reactor/reaction chamber and separating unit for the removal of ammonia/alcohol from the product mixture are separated from one another. This has the advantage that different pressure ranges can be employed for the reaction of the reactants and the subsequent removal of ammonia/alcohol. The separation of the process into a reaction step in the pressure reactor under higher pressure than in a separating step in a pressure column, both steps being conducted under elevated pressure, i.e. greater than 1 bar, succeeds, in a not immediately foreseeable manner, in addition to the advantages addressed to date in the first variant in the process according to the invention, in once again significantly improving the separating action and of increasing the efficiency of the removal of the ammonia/alcohol mixture.

The quality features mentioned can be improved even further by repeating the reaction in the pressure reactor once or more than once with the product mixture depleted in ammonia and alcohol in the bottom of the separating column (pressure distillation column), the reaction step being shifted to a multitude of pressure reactors connected in series.

In this regard, very particular preference is given to a process variant which is characterized in that
e) the product mixture discharged in step d1) is compressed to a pressure in the range of 5 to 70 bar;
f) the mixture compressed in the manner according to step e) is fed into a further pressure reactor for reaction and allowed to react again; and
g) steps b2), c1), c2) and d1) are repeated according to the abovementioned enumeration.

Accordingly, it is of particular interest that the mixture depleted in ammonia and alcohol is withdrawn from a tray above the bottom of the first distillation column, compressed to a pressure greater than in the distillation column and then fed into a second pressure reactor, whence, after another reaction under the action of elevated pressure and temperature to obtain a twice-reacted product mixture, it is decompressed back to a pressure less than in the second pressure reactor and greater than 1 bar, and then recycled into the first distillation column below the tray from which the feed into the second pressure reactor was effected but above the bottom of the first distillation column, where ammonia and alcohol are again distilled off via the top to obtain a mixture twice depleted in ammonia and alcohol.

This process step can be repeated as desired; for example, three to four repetitions are particularly favourable. In this regard, preference is given to a process which is characterized in that the reaction in the pressure reactor, the decompression of the reacted mixture, the feeding into the first distillation column, the depletion of ammonia and alcohol in the first distillation column, the withdrawal of the depleted mixture, compression and feeding of the depleted mixture into a further pressure reactor, are repeated more than once, to obtain at the bottom of the pressure distillation column, a product mixture which has been depleted n times in ammonia and alcohol according to the number n of pressure reactors connected in series. n may be a positive integer greater than zero. n is preferably in the range of 2 to 10.

An appropriate process modification envisages that the aforementioned steps e) to g) defined above are repeated more than once.

Very specific process variants include the performance of the reaction and depletion four times using four pressure reactors connected in series to obtain a product mixture depleted four times in ammonia and alcohol. This process variant is accordingly characterized in that steps e) to g) are repeated at least twice more, so that the reaction is performed in a total of at least four series-connected pressure reactors.

In this connection, it is obvious to those skilled in the art that a sufficient amount of alcohol is present in each reaction step. Therefore, the product mixture is preferably depleted only partially in alcohol. On the other hand, the alcohol can also be added separately to the particular reaction.

For the given process variant, different temperature ranges in the column and the reactor have been found to be particularly appropriate.

In the process variant described above, the reaction in step c) can be performed at a higher pressure than the distillation of the ammonia in step d). The difference in pressure is preferably at least 10 bar, more preferably at least 40 bar and most preferably at least 50 bar.

For instance, the pressure distillation column generally and preferably has a temperature in the range of about 50° C. to about 160° C. The exact temperature is established typically by the boiling system depending on the pressure conditions existing.

The temperature in the reactor is preferably in the range of about 120° C.-240° C. It is very particularly appropriate to lower the temperature from reactor to reactor, for example in steps in the range of 3-15° C., preferably 4-10° C. and very particularly appropriately in steps of 5° C. This positively influences the selectivity of the reaction.

A further measure for increasing the selectivity may also consist in reducing the reactor volume from reactor to reactor. With decreasing reactor volume at increasing conversion, an improved selectivity is likewise obtained. The reduction in the reactor volume may preferably be in the range of 1% to 50%, more preferably 2% to 20% and most preferably 5% to 10%, based on the volume of the larger reactor in each case.

The various measures for increasing the selectivity can be combined particularly advantageously. Thus, the person skilled in the art can optimize the selectivity in a simple manner by varying pressure, temperature and residence time. More preferably, the reaction can, for example, be effected at a temperature in the range of 200 to 220° C., and the residence time can be optimized. The removal of ammonia from the reaction mixture allows the reaction to be repeated several times, and this allows particularly appropriate reaction control, i.e. high selectivity at low costs, to be achieved.

As already mentioned above, it is favourable to withdraw the product mixture to be withdrawn from the pressure distillation column at certain points in the column. For orientation, the distance of the withdrawal point from the bottom (column bottom) of the column is used as a relative statement of position. In the context of the invention, the procedure is particularly appropriately to feed in the decompressed product mixture of step c1), after each further reaction in a pressure reactor, more closely adjacent to the bottom of the distillation column, based on the feed point of the feed of the preceding step c1).

This process variant can advantageously feature performance of the reaction in step b) at a pressure in the range of 20 bar to 90 bar, more preferably 40 bar to 80 bar and most preferably 50 bar to 70 bar.

The ammonia can be distilled in step d) preferably at a pressure in the range of 1.2 bar to 10 bar, more preferably 1.5 bar to 3 bar.

In addition to the variant described, in which the reaction of the alpha-hydroxycarboxamide with the alcohol is performed separately from the removal of the ammonia which results therein, among other products, in two spatially separate but connected units, it may be preferred in a further process modification to undertake the reaction step and the removal step in a single apparatus. Pressure reactor and pressure distillation column are realized in a single unit, and effectively coincide.

In this particular embodiment of the invention, this includes continuous processes for preparing alpha-hydroxycarboxylic esters in which the reactants reacted are alpha-hydroxycarboxamide with an alcohol in the presence of a catalyst to obtain a product mixture which comprises alpha-hydroxycarboxylic ester, ammonia, unconverted alpha-hydroxycarboxamide and also alcohol and catalyst; in this process, a') reactant streams comprising, as reactants, an alpha-hydroxycarboxamide, an alcohol and a catalyst are fed into a pressure reactor;

b') the reactant streams are reacted with one another in the pressure reactor at a pressure in the range of 1 bar to 100 bar;

c') the product mixture is depleted in alcohol and ammonia by distilling off ammonia at a pressure which is constantly kept greater than 1 bar without the aid of additional stripping media; and d') the product mixture which results from step c'), has been depleted in ammonia and alcohol and comprises alpha-hydroxycarboxylic ester, unconverted alpha-hydroxycarboxamide and catalyst is discharged from the pressure reactor.

The pressure range to be observed in the above-described variant of the invention, preferably in a reactive distillation column serving as the reactor, is variable over wide ranges. A preferred embodiment of the invention encompasses the performance of steps a') to c') simultaneously in a reactive distillation column at a pressure in the range of 2 bar to 50 bar, preferably 5 bar to 40 bar. A particularly favourable process is one in which steps a') to c') are performed simultaneously in a reactive distillation column at a pressure in the range of 10 bar to 30 bar.

In a preferred variant of the process according to the invention, the reaction of the reactants is performed in a reactive distillation column designed as a pressure column, and the ammonia formed is distilled off continuously via the top of the column during the reaction. This achieves the surprising effect that ammonia can be removed and recovered in high purity in a very simple manner without needing to reduce the pressure. Also of particular interest in this context is a variant in which ammonia is distilled off under pressure via the top of the column, and the alcohol is removed from the column via the bottom or via a sidestream. An appropriately adjusted separating action of the reactive distillation column thus achieves immediate separation of ammonia and alcohol.

The reaction temperature of the inventive reactions can vary over a wide range, the reaction rate generally increasing with increasing temperature. The upper temperature limit arises generally from the boiling point of the alcohol used.

The reaction temperature is preferably in the range of 40-300° C., more preferably 120-240° C. and most preferably 180° C. to 220° C.

For the invention, it may be advantageous when at most 10% by weight, preferably at most 5% by weight and more preferably at most 1% by weight of the alcohol present in the reaction phase is removed from the reaction system via the gas phase. This measure allows the reaction to be performed particularly inexpensively. In this context, the reaction system is advantageously notable in that it is kept constantly under a pressure of greater than 1 bar. In this case, the reaction system may comprise in particular the regions of the system in which the reaction proceeds and the regions of the system in which the ammonia is removed from the products and the alcohol, especially the distillation columns. Accordingly, the separation of ammonia and alcohol can preferably be effected at a pressure of greater than 1 bar, more preferably greater than 1.5 bar, with a very high efficiency. In this context, it may be particularly appropriate that at most 10% by weight of the alcohol, based on the alcohol supplied within the residence time, is distilled out of the reaction system together with the ammonia.

The residence time may preferably be 30 seconds to 2 hours, more preferably 1 minute to 30 minutes and most preferably 2 minutes to 15 minutes. These data are preferably based on the reactor volume. In the case of a plurality of reactors, the sum of the volumes of the pressure reactors is employed, without including the volume of the distillation apparatus. When reactive stills also are used, the residence times are calculated correspondingly from the volume of the reactive still.

For the present invention, in one variant, any multistage pressure-resistant distillation column which preferably has two or more separating stages can be used. In the present invention, the number of separating stages refers to the number of trays in a tray column or the number of theoretical plates in the case of a column with structured packing or a column with random packing.

Examples of a multistage distillation column with trays include those such as bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as Mellapak (Sulzer), Rombopak (Kühni), Montz-Pak (Montz), and structured packings with catalyst pockets, for example Kata-Pak.

A distillation column with combinations of regions of trays, of regions of random packings or of regions of structured packings can likewise be used.

The product mixture depleted in ammonia comprises, inter alia, the desired alpha-hydroxycarboxylic ester. For further isolation and purification of the ester, it is possible, in an appropriate process modification, to draw off the product mixture depleted in ammonia via the bottom of the distillation column and to feed it to a further second distillation column, where the alcohol is distilled off via the top of the column to obtain a mixture depleted both in ammonia and in alcohol, and preferably recycled into a reactor.

For further isolation and recovery of the alpha-hydroxycarboxylic ester from the mixture depleted in ammonia and alcohol, preference is then given to a process in which the mixture depleted in ammonia and alcohol is discharged via the bottom of the further distillation column and fed to yet a further distillation column in which the alpha-hydroxycarboxylic ester is distilled off via the top, and the thus obtained mixture depleted in ammonia, alcohol and alpha-hydroxycarboxylic ester, if appropriate after further purification steps, is recycled into the reactor. The alpha-hydroxycarboxylic ester product obtained via the top of the column is highly pure and can, for example, be fed extremely advantageously to further reaction steps for obtaining alkyl (meth)acrylates.

As outlined, the distillation apparatus preferably has at least one region, known as reactor, in which at least one catalyst is provided. This reactor may, as described, preferably be within the distillation column.

In the context of the invention, it has been found that the procedure outlined can tolerate a large spectrum of quantitative ratios of the reactants. For instance, the alcoholysis can be performed at a relatively large alcohol excess or deficiency compared to the alpha-hydroxycarboxamide. Particular preference is given to processes in which the reaction of the reactants is undertaken at a molar starting ratio of alcohol to alpha-hydroxycarboxamide in the range of 1:3 to 20:1. The ratio is very particularly appropriately 1:2 to 15:1 and even more appropriately 1:1 to 10:1.

Preference is further given to processes which are characterized in that the alpha-hydroxycarboxamide used is hydroxyisobutyramide and the alcohol used is methanol.

The reaction according to the invention takes place in the presence of a catalyst. The reaction can be accelerated, for example, by basic catalysts. These include homogeneous catalysts and heterogeneous catalysts.

Catalysts of very particular interest for the performance of the process according to the invention are lanthanoid compounds, particular preference being given to water-stable lanthanoid compounds. The use of this type of homogeneous catalysts in a process of the invention is novel and leads to surprisingly advantageous results. The term "water-stable" means that the catalyst retains its catalytic properties in the presence of water. Accordingly, the inventive reaction can be effected in the presence of up to 2% by weight of water without this significantly impairing the catalytic ability of the catalyst. In this context, the expression "significantly" means that the reaction rate and/or the selectivity decreases at most by 50%, based on the reaction without the presence of water.

Lanthanoid compounds refer to compounds of La, Ce, Pr, Nd, Pm, Sm, Eu, Gd, Td, Dy, Ho, Er, Tm, Yb and/or Lu. Preference is given to using a lanthanoid compound which comprises lanthanum.

The lanthanoid compound preferably has a solubility in water of at least 1 g/l, preferably at least 10 g/l, at 25° C.

Preferred lanthanoid compounds are salts which are preferably present in the oxidation state of 3.

Particularly preferred water-stable lanthanoid compounds are $La(NO_3)_3$ and/or $LaCl_3$. These compounds may be added to the reaction mixture as salts or be formed in situ.

Further homogeneous catalysts useable successfully in the present invention include alkali metal alkoxides and organometallic compounds of titanium, tin and aluminium. Preference is given to using a titanium alkoxide or tin alkoxide, for example titanium tetraisopropyloxide or tin tetrabutyloxide.

A particular process variant includes the use, as the catalyst, of a soluble metal complex which comprises titanium and/or tin and the alpha-hydroxycarboxamide.

Another specific modification of the process of the invention envisages that the catalyst used is a metal trifluoromethanesulphonate. Preference is given to using a metal trifluoromethanesulphonate in which the metal is selected from the group consisting of the elements in groups 1, 2, 3, 4, 11, 12, 13 and 14 of the periodic table. Among these, preference is given to using those metal trifluoromethanesulphonates in which the metal corresponds to one or more lanthanoids.

In addition to the preferred variants of homogeneous catalysis, processes using heterogeneous catalysts are also appropriate under some circumstances. The heterogeneous catalysts useable successfully include magnesium oxide, calcium oxide and basic ion exchangers and the like.

For example, preference may be given to processes in which the catalyst is an insoluble metal oxide which contains at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi.

Alternatively, preference may be given to processes in which the catalyst used is an insoluble metal selected from the group consisting of Ti, Zr, Hf, V, Nb, Ta, Cr, Mo, W, Fe, Co, Ni, Cu, Ga, In, Bi and Te.

The ammonia released in the alcoholysis in the process of the invention can then, for example, be recycled in a simple manner to an overall process for preparing alkyl (meth)acrylates. For example, ammonia can be reacted with methanol to give hydrocyanic acid. This is detailed, for example, in EP-A-0941984. In addition, the hydrocyanic acid can be obtained from ammonia and methane by the BMA or Andrussow process, these processes being described in Ullmann's Encyclopaedia of Industrial Chemistry 5th edition on CD-ROM, under "Inorganic Cyano Compounds". The ammonia can likewise be recycled into an ammoxidation process, for example the industrial scale synthesis of acrylonitrile from ammonia, oxygen and propene. The acrylonitrile synthesis is described under "Sohio Process" in Industrial Organic Chemistry by K. Weisermehl and H.-J. Arpe on page 307 ff.

Figure 1:
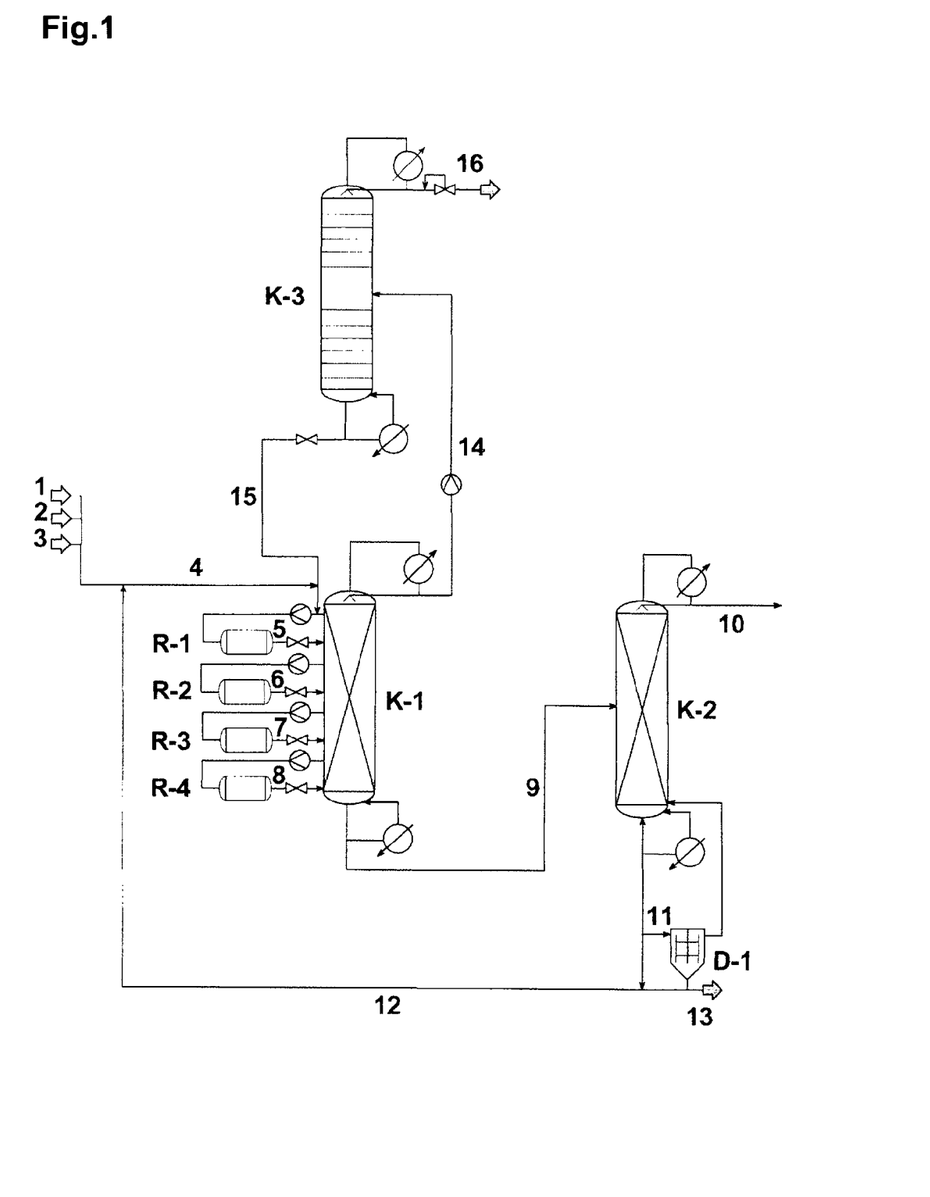
FIG. 1 shows a combination of a pressure rectification column and pressure reactors.

General process operation of a first variant of the invention with reference to FIG. 1

In a particularly preferred embodiment, the alcoholysis, preferably methanolysis, can be effected in the combination of a pressure rectification column and several pressure reactors shown in FIG. 1. The hydroxyisocarboxamide, for example hydroxyisobutyramide, is fed to a first pressure reactor (R-1) via line (1), together with methanol via line (2) and a methanol/catalyst mixture via line (3), through line (4). Under the aforementioned reaction conditions, a reaction mixture composed of the hydroxyisocarboxylic ester and ammonia, unconverted hydroxyisocarboxamide and methanol, catalyst and traces of a by-product forms in the reactor (R-1). After leaving the reactor (R-1), this mixture is decompressed to a lower pressure level and passed via line (5) into a pressure column (K-1). The column is preferably equipped with structured packings. The ammonia is separated there from the reaction mixture with a portion of the methanol and obtained as distillate at the top. The higher-boiling components, the hydroxyisocarboxylic ester, the by-product and the unconverted hydroxyisobutyramide, are drawn back out of the column with the remaining methanol, compressed to reactor pressure and fed to the 2nd pressure reactor (R-2). The reaction is effected preferably in 4 pressure reactors connected in series (R-1 to R-4). The product mixture which leaves the column (K-1) via the bottom consists of the hydroxyisocarboxylic ester, traces of a by-product and the hydroxyisobutyramide. It is passed into the still (K-2) through line (9). The hydroxyisocarboxylic ester is obtained there as the distillate and is drawn off via the line (10). The hydroxyisocarboxamide/catalyst mixture leaves the column (K-2) via the bottom and is passed partially via lines (12) and (4) back into the first pressure reactor (R-1). A part-stream (11) is fed to a thin-film evaporator (D-1). This enables the discharge of a mixture of amide, the high-boiling by-product and the catalyst via the line (13).

The ammonia/methanol mixture obtained as the distillate in the column (K-1) is compressed and fed via line (14) to a further column (K-3). This separates the ammonia, which is obtained in pure form at the top, from the methanol, which is recycled via lines (15) and (4) into the first pressure reactor (R1).

| Reaction conditions, column + 4 external reactors | |
|---|---|
| Temperature [° C.] | 120-240 |
| Reactor pressure [bar] | 5-70 |
| Column pressure [bar] | 1-10 |
| $n_{CH3OH}:n_{amide}$ | 1:3-20:1 |

Figure 2:
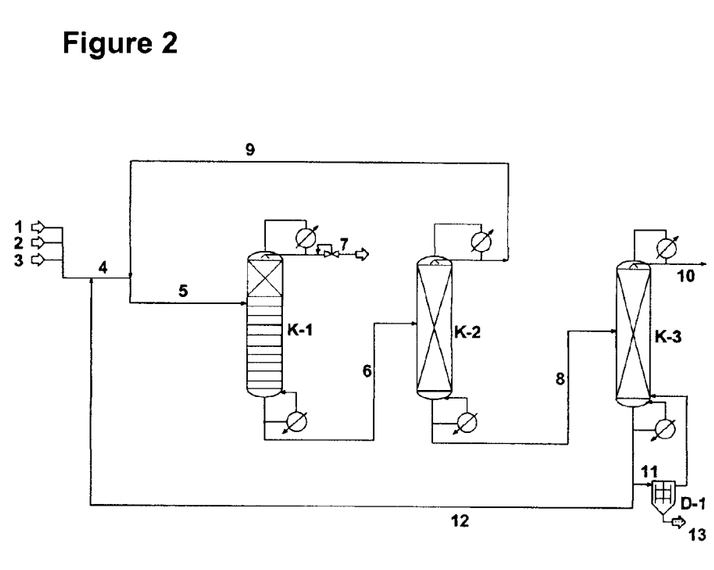
FIG. 2 shows a plant for operating an embodiment of the invention.

General process operation of a second variant of the invention with reference to FIG. 2

For example, the alcoholysis, preferably methanolysis, can be effected in the plant shown in FIG. 2. The hydroxyisocarboxamide, for example hydroxyisobutyramide, is fed to a reactive distillation column (K-1) via line (1), together with methanol via line (2) and a methanol/catalyst mixture via line (3). The column is designed as a pressure column and is preferably equipped with trays. Under the aforementioned reaction conditions, a reaction mixture composed of hydroxyisocarboxylic ester and ammonia, unconverted hydroxyisocarboxamide and methanol, catalyst and traces of a by-product forms on the trays of the column. The ammonia is obtained as the distillate and is drawn off via line (7). The high-boiling components, the hydroxyisocarboxylic ester, the by-product and the unconverted hydroxyisobutyramide and methanol reactants, leave the column via the bottom. This mixture is passed via line (6) into a further still (K-2). In this column, methanol is obtained as a distillate, which can be conducted through lines (9) and (5) back into the column (K-1). The mixture of the hydroxyisocarboxylic ester, the by-product and the hydroxyisobutyramide obtained from the bottom is passed through line (8) into the still (K-3). The hydroxyisocarboxylic ester is drawn via line (10) as distillate. The hydroxyisocarboxamide/catalyst mixture leaves the column via the bottom and is passed partially through lines (12), (4) and (5) back into the column (K-1). A part-stream (11) is fed to a thin-film evaporator (D-1). This enables the discharge of a mixture of amide, high boilers and catalyst via line (13).

| Reaction conditions, pressure reactive distillation column: | |
|---|---|
| Temperature [° C.] | 120-240 |
| Column pressure [bar] | 2-40, preferably 5-30 |
| $n_{CH3OH}:n_{amide}$ | 1:3-20:1 |

The present invention will be illustrated in detail hereinafter with reference to examples.

EXAMPLES

Example 1

In a laboratory test plant consisting of a reactant feed and a continuous stirred tank reactor, 157 g/h of a methanol/catalyst mixture with a catalyst content of 0.8% by weight and 35 g/h of alpha-hydroxyisobutyramide were fed in over an experiment time of 48 h. The reaction was performed using $La(NO_3)_3$ as the catalyst. The product mixture formed was analysed by means of gas chromatography. The molar selectivity for methyl alpha-hydroxyisobutyrate based on alpha-hydroxyisobutyramide was 98.7%, and an ammonia concentration in the product mixture of 0.7% by weight was found.

Examples 2-7

Table 1 shows further examples which were performed in the test apparatus specified at a molar reactant ratio of MeOH: HIBA of 14:1, but at different reaction temperatures and residence times.

TABLE 1

| Example | Reaction temperature [° C.] | Residence time [min] | Selectivity for MHIB [%] | % by weight [NH₃] |
|---|---|---|---|---|
| 2 | 200 | 5 | 95 | 0.356 |
| 3 | 220 | 5 | 98 | 0.588 |
| 4 | 180 | 10 | 92 | 0.154 |
| 5 | 200 | 10 | 94 | 0.285 |
| 6 | 200 | 30 | 89 | 0.611 |
| 7 | 220 | 30 | 89 | 0.791 |

Table 1 makes it clear that the selectivity for MHIB (methyl α-hydroxyisobutyrate) depends not only on the ammonia concentration in the reaction mixture in the reactor but also on the reaction parameters of residence time and temperature and hence on exact reaction control.

Example 8

In the laboratory test plant mentioned, a methanol/catalyst mixture with a catalyst content of 1.0% by weight and alpha-hydroxyisobutyramide in a molar ratio of 7:1 were metered in continuously over an experiment time of 48 h. The conversion to MHIB and ammonia was effected at a pressure of 75 bar and a reaction temperature of 220° C. with a residence time of 5 min. The reaction was performed using $La(NO_3)_3$ as the catalyst. The product mixture formed was analysed by means of gas chromatography. The molar selectivity for methyl alpha-hydroxyisobutyrate based on alpha-hydroxyisobutyramide was 99%, and an ammonia concentration in the product mixture of 0.63% by weight was found.

Examples 9-12

In the laboratory test plant mentioned, a methanol/catalyst mixture with a catalyst content of 0.9% by weight and alpha-hydroxyisobutyramide in a molar ratio of 10:1 were metered in continuously over an experiment time of 48 h. The conversion to MHIB and ammonia was effected at a pressure of 75 bar and a reaction temperature of 200 and 220° C. with a residence time of 5 min or 10 min. The reaction was performed using $La(NO_3)_3$ as the catalyst. The product mixture formed was analysed by means of gas chromatography. The molar selectivity for methyl alpha-hydroxyisobutyrate based on alpha-hydroxyisobutyramide and the ammonia concentration in the product mixture are listed in Table 2.

TABLE 2

| Example | Reaction temperature [° C.] | Residence time [min] | Selectivity for MHIB [%] | % by weight [NH$_3$] |
|---|---|---|---|---|
| 9 | 200 | 5 | 97 | 0.429 |
| 10 | 220 | 5 | 98 | 0.73 |
| 11 | 200 | 10 | 98 | 0.544 |
| 12 | 220 | 10 | 96 | 0.889 |

The invention claimed is:

1. A continuous process for preparing an alpha-hydroxycarboxylic ester, comprising:
reacting an alpha-hydroxycarboxamide with an alcohol in the presence of the catalyst to obtain a product mixture which comprises the alpha-hydroxycarboxylic ester, ammonia, the alpha-hydroxycarboxamide, the alcohol, and the catalyst;
wherein
a) reactant streams comprising, the alpha-hydroxycarboxamide, the alcohol and the catalyst are fed into a pressure reactor;
b) the reactants are reacted with one another in the pressure reactor at the pressure of from greater than 1 bar to 100 bar to form the product mixture; and
c) the ammonia in the product mixture is depleted by distilling off ammonia and alcohol at a pressure which is less than the pressure of the reaction and greater than 1 bar without an addition of a stripping media.

2. The process according to claim 1, wherein
c) the product mixture is discharged from the pressure reactor; and
then the distillation of the ammonia and the alcohol at a pressure greater than 1 bar and less than the reaction pressure is conducted.

3. The process according to claim 2, wherein
the pressure in the pressure reactor is from 5 bar to 70 bar;
the product mixture discharged from the pressure reactor is decompressed to a pressure lower than the pressure in the pressure reactor and greater than 1 bar;
the decompressed product mixture is fed into a distillation column;
ammonia and the alcohol are distilled off via the top in the distillation column, while the pressure in the distillation column is maintained greater than 1 bar to less than 10 bar; and
the product mixture depleted in ammonia is discharged from the column.

4. The process according to claim 3, wherein the process further comprises:
compressing the product mixture discharged from the column to a pressure of 5 to 70 bar;
feeding the compressed product mixture into a further pressure reactor; reacting unconverted alpha-hydroxycarboxamide with unconverted alcohol in the presence of the catalyst; and
repeating the decompression, distillation and discharge operations.

5. The process according to claim 4, wherein the compression, reaction, decompression and distillation operations are repeated more than once.

6. The process according to claim 5, wherein the compression, reaction, decompression and distillation operations are repeated at least twice more, so that the process is performed in a total of at least four pressure reactors connected in series.

7. The process according to claim 4, wherein the decompressed product mixture is fed in more closely adjacent to the bottom of the distillation column, based on the feed point of the feed of the preceding decompressed feed.

8. The process according to claim 4, wherein the temperature is lowered from each previous reactor to each successive reactor.

9. The process according to claim 8, wherein the lowering of the temperature is in the range of 3 to 15° C.

10. The process according to claim 4, wherein the reactor volume is reduced from each previous reactor to each successive reactor.

11. The process according to claim 10, wherein the reduction in the reactor volume is in the range of 2% to 20%, based on the volume of the larger reactor in each case.

12. The process according to claim 1, wherein the pressure of the pressure reactor is at least 40 bar greater than the distillation pressure.

13. The process according to claim 2, wherein the distillation of the ammonia is effected at a pressure in the range of 1.5 bar to 3 bar.

14. The process according to claim 2, wherein the reaction is performed at a pressure in the range of 50 to 70 bar.

15. The process according to claim 1, wherein the compression, reaction, decompression and distillation operations are performed simultaneously in one reactive distillation column at a pressure of 5 bar to 40 bar.

16. The process according to claim 15, wherein the pressure is from 10 bar to 30 bar.

17. The process according to claim 15, wherein ammonia is distilled off via the top of the column under pressure, and the alcohol is removed from the column via the bottom or via a sidestream of the column.

18. The process according to claim 15, wherein a molar starting ratio of the alcohol to the alpha-hydroxycarboxamide is from 1:3 to 20:1.

19. The process according to claim 15, wherein the alpha-hydroxycarboxamide is α-hydroxyisobutyramide, α-hydroxyisopropionamide or a mixture thereof.

20. The process according to claim 19, wherein the alpha-hydroxycarboxamide is hydroxyisobutyramide and the alcohol is methanol.

21. The process according to claim 15, wherein the temperature of the reaction is from 120 to 240° C.

22. The process according to claim 15, wherein the residence of the reactants in the reactor is from 1 to 30 minutes.

23. The process according to claim 22, wherein the residence time is from 2 to 15 minutes.

24. The process according to claim 15, wherein at most 10% by weight, based on the weight of alcohol supplied to the reactor, is distilled out of the reaction system together with the ammonia within the residence time in the reactive distillation column.

25. The process according to claim 15, wherein the catalyst comprises at least one lanthanoid compound.

26. The process according to claim 25, wherein the at least one lanthanoid compound is stable to water.

27. The process according to claim 25, wherein the at least one lanthanoid compound is a salt.

28. The process according to claim 25, wherein the at least one lanthanoid compound is in the III oxidation state.

29. The process according to claim 25, wherein the water solubility of the at least one lanthanoid compound is at least 10 g/l.

30. The process according to claim 25, wherein the at least one lanthanoid compound comprises lanthanum.

31. The process according to claim 30, wherein the lanthanoid compound comprises La(NO$_3$)$_3$ or LaCl$_3$.

32. The process according to claim 15, wherein the catalyst is a soluble metal complex which comprises at least one of titanium and tin and the alpha-hydroxycarboxamide.

33. The process according to claim 15, wherein the catalyst is a metal trifluoromethanesulphonate.

34. The process according to claim 33, wherein the metal of the metal trifluoromethanesulphonate is one selected from the group consisting of the elements in groups 1, 2, 3, 4, 11, 12, 13 and 14 of the periodic table.

35. The process according to claim 34, wherein the metal of the metal trifluoromethanesulphonate is at least one lanthanoid.

36. The process according to claim 15, wherein the catalyst is an insoluble metal oxide which comprises at least one element selected from the group consisting of Sb, Sc, V, La, Ce, Ti, Zr, Hf, V, Nb, Ta, Cr, Mo, W, Tc, Re, Fe, Co, Ni, Cu, Al, Si, Sn, Pb and Bi.

37. The process according to claim 15, wherein the catalyst is an insoluble metal selected from the group consisting of Ti, Zr, Hf, V, Nb, Ta, Cr, Mo, W, Fe, Co, Ni, Cu, Ga, In, Bi and Te.

\* \* \* \* \*